United States Patent [19]

Iwamoto et al.

[11] 4,230,067
[45] Oct. 28, 1980

[54] LIQUID APPLYING APPARATUS

[75] Inventors: Taro Iwamoto; Shimon Ando; Koji Kurokawa; Sho Kusumoto, all of Hitachi, Japan

[73] Assignee: Hitachi, Ltd., Japan

[21] Appl. No.: 942,559

[22] Filed: Sep. 15, 1978

[30] Foreign Application Priority Data

Sep. 17, 1977 [JP]   Japan ................................. 52-111768
Jan. 27, 1978 [JP]   Japan ................................. 53-7207
Feb. 8, 1978 [JP]    Japan ................................. 53-12456

[51] Int. Cl.$^3$ ............................................. B05C 1/02
[52] U.S. Cl. ..................................... 118/104; 118/109; 118/120; 118/203; 118/206; 118/263; 118/323; 118/264; 15/102
[58] Field of Search ............... 118/120, 323, 203, 264, 118/242, 243, 104, 263, 109, 206, 304; 15/102, 116 A

[56] References Cited

U.S. PATENT DOCUMENTS

| 426,135 | 4/1890 | Murphy et al. | 118/203 X |
| 1,433,976 | 10/1922 | Weightman et al. | 118/203 |
| 1,619,961 | 3/1927 | Abbott | 15/102 X |
| 3,117,026 | 1/1964 | Spier | 118/243 X |
| 3,719,133 | 3/1973 | Haracz | 118/120 X |

FOREIGN PATENT DOCUMENTS

49-34623  9/1974  Japan .
50-15591  2/1975  Japan .

*Primary Examiner*—John P. McIntosh

*Attorney, Agent, or Firm*—Craig & Antonelli

[57] ABSTRACT

Apparatus for applying liquids including a main body and a carrier supporting the main body for movement, the main body having mounted therein conduits and charge-over valves for supplying liquids, and spray nozzles for spraying the liquids in predetermined amounts onto a liquid-absorptive, resilient contacting member to enable the latter to apply the liquids to a surface by sliding rubbing contact therewith as the carrier is actuated or for spraying the liquids directly onto the surface. The liquids absorbed by the contacting member are squeezed therefrom when a surface cleaning operation or a liquid applying operation is completed or any time the contacting member is soiled, by bringing the contacting member into pressing engagement with a liquid receiving pan. The contacting member may be in the form of a cylinder and mounted at a forward end of a hollow shaft rotatably connected to the carrier, so that the contacting member can be brought into rubbing sliding contact with the surface to apply the liquids thereto or can be covered with a movable cover to remove absorbed liquids by centrifugal forces. The conduits for supplying the liquids are connected to tanks containing the liquids and divided into a cleaning liquid feeding system and an applied liquid feeding system, and the change-over valves are capable of switching the apparatus between the two systems. The main body is capable of movement in a three dimensional space determined by the movement of various elements of the carrier in the directions of the X, Y and Z axes.

14 Claims, 8 Drawing Figures

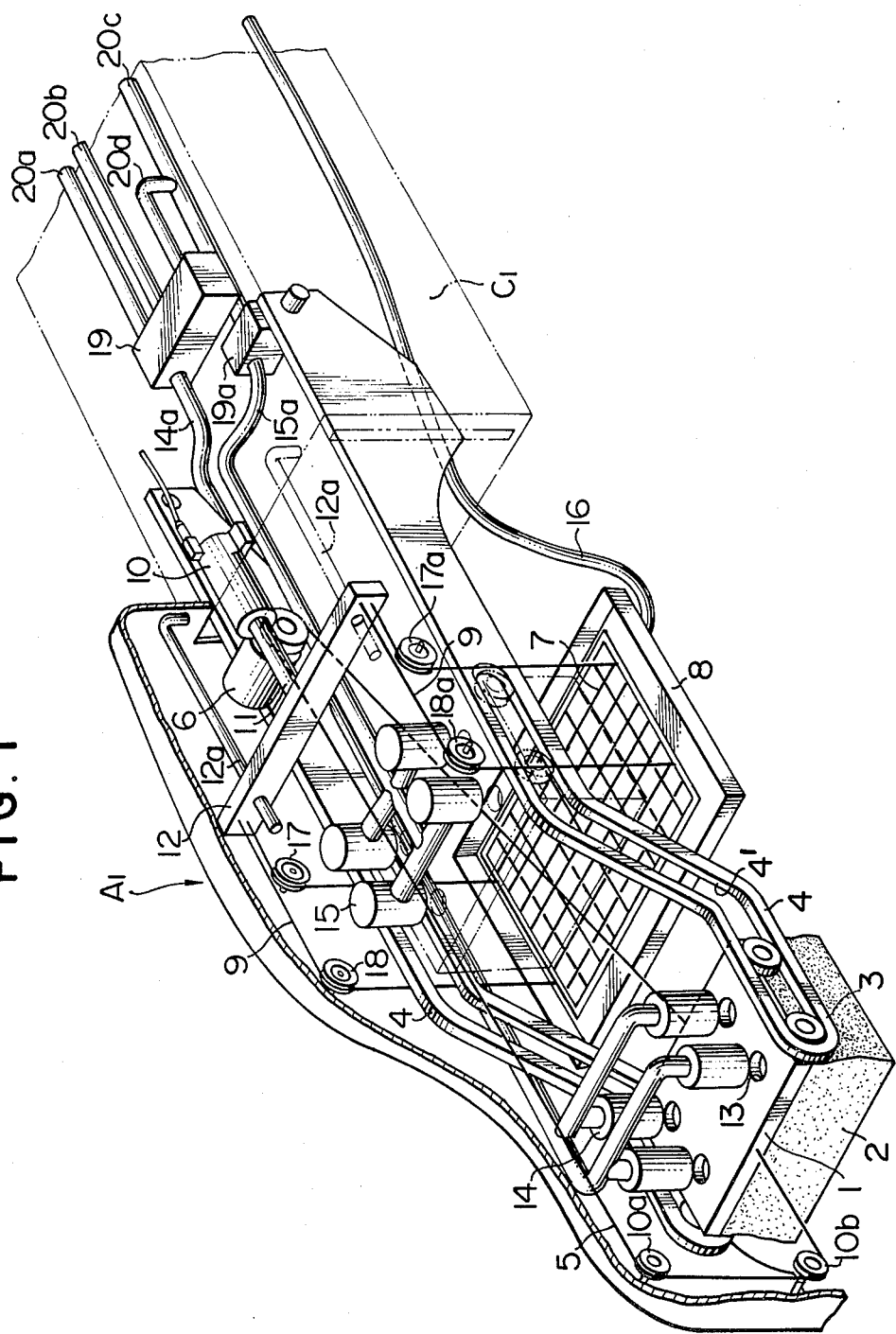

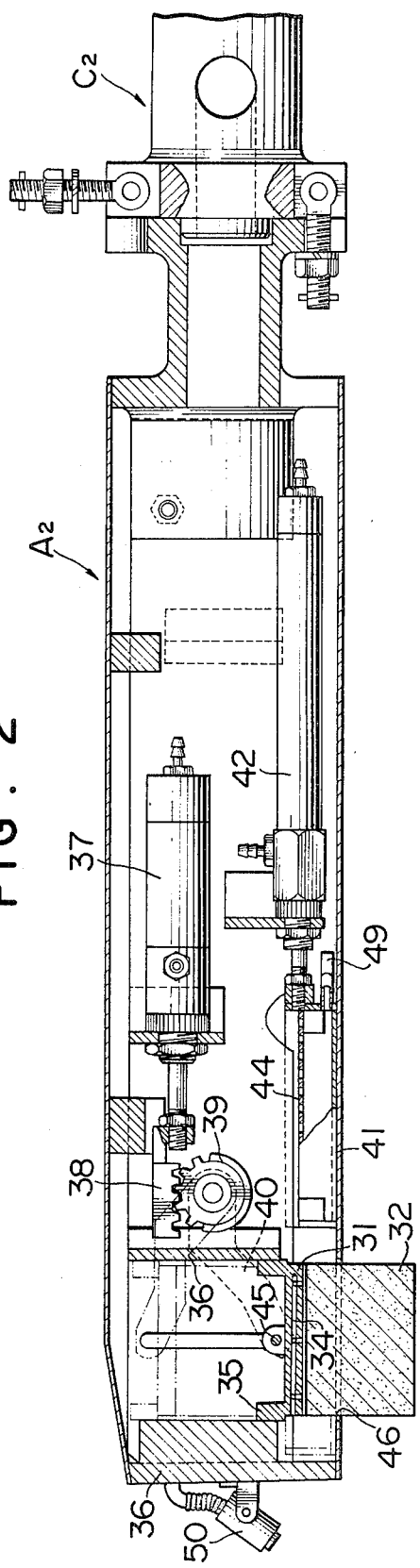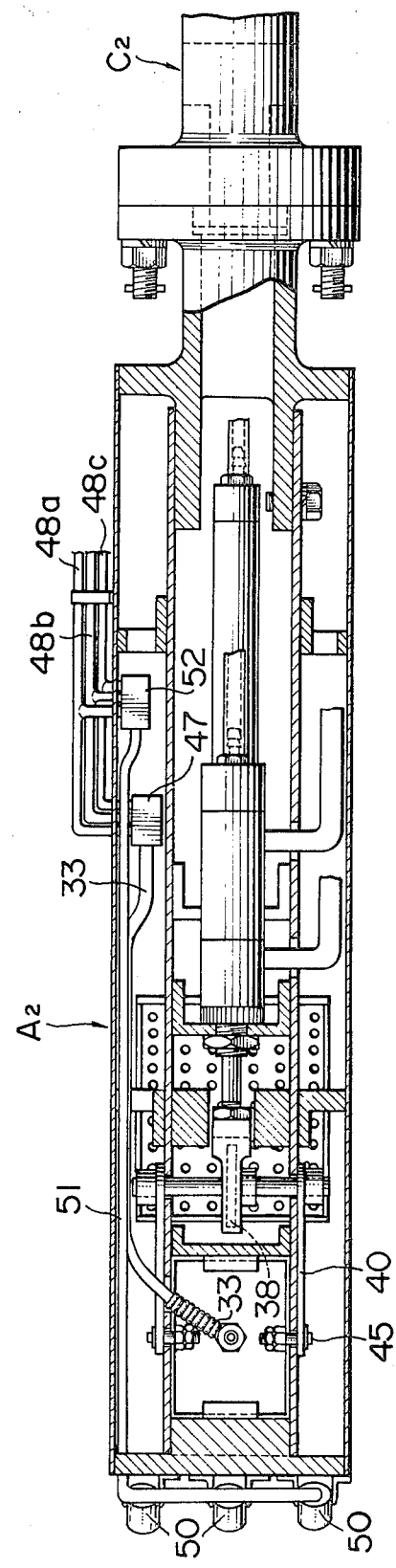

LIQUID APPLYING APPARATUS

BACKGROUND OF THE INVENTION

This invention relates to apparatus for automatically applying, as by rubbing or spraying, a liquid agent to the surface of an article to be tested and for wiping, if necessary the applied liquid agent, and more particularly to an apparatus for automatically applying, as by rubbing or spraying, a plurality of liquid agents in optimum amounts to the surface of an immovable structure when a non-destructive test for detecting defects in the structure is carried out and for wiping these liquid agents, if necessary, from the surface of the structure.

Generally, difficulties are encountered in detecting, by naked eyes, fine fissures or pinholes on the surface of an article. It is common practice to use a variety of non-destructive testing methods for detecting the presence or absence of surface defects in a tested article. Of all the non-destructive testing methods, a penetration test for detecting defects has hitherto been widely used, because this method is relatively easy to practice and yet capable of detecting defects with a relatively high degree of precision.

In carrying out the penetration test for detecting defects, a penetrating liquid is applied, as by rubbing or spraying, to the surface of an article to be tested so as to cause the penetrating liquid to find its way into defects, for example, and then the penetrating liquid applied to the surface of the article to be tested is wiped, or the surface of the article coated with the penetrating liquid is dried and a finishing liquid is applied to the surface. In this way, defects on the surface of the article to be tested are colored and recognized by naked eyes.

It has hitherto been customary to apply the penetrating liquid and finishing liquid manually, when the penetration test for detecting defects is carried out. Therefore, this testing method has not hitherto been carried out satisfactorily when there are many surfaces to be tested. Manual application of liquids to a lot of surfaces is carried out only with low efficiency. Moreover, when liquid application is carried out manually, it is impossible to equalize the amounts of liquid applied to various surfaces, and there is a tendency to apply the liquid in an amount which is greater than is necessary.

A penetration test for detecting defects has been described in U.S. Pat. Nos. 3,762,216, 3,926,044 and 3,341,010, Japanese Patent Application Laid-Open No. 15591/75 and Japanese Patent Publication No. 34623/74, for example. The apparatus disclosed in the prior art for carrying out this testing method are all intended for use in movable structures or articles. These apparatus are not adapted for use in testing immovable structures, or a great difficulty is experienced in applying these apparatus to the testing of immovable structures. Moreover, these apparatus have the disadvantage that the amount of the liquid applied to the surface of a structure to be tested sometimes becomes too great, because the liquid is applied by spraying through nozzles and other means to the surface to be tested, with the result that the consumption of the penetrating liquid is high. Another problem encountered with regard to the apparatus of the prior art is that, when the liquid is applied in excess to a portion of a surface from which excess liquid cannot be removed, the liquid collects in this portion and means must be provided for removing excess liquid from this portion in order to efficiently carry out the test.

SUMMARY OF THE INVENTION

This invention has as its object the provision of an apparatus for automatically applying, as by rubbing or spraying, in optimum amounts a variety of liquids, including a cleaning liquid, a penetrating liquid, and a finishing liquid, to the surface of an immovable structure and for removing, if necessary, as by rubbing off, the liquids applied to the surface to be tested.

According to the invention, there is provided an automated apparatus which is capable of automatically carrying out a non-destructive test relying on penetration of the surface of an immovable structure with a pentrating liquid and of applying, as by rubbing or spraying, a variety of liquids to all parts of the surface to be tested without consuming liquids in amounts greater than is necessary, while being able, if necessary, to remove the applied liquids, as by rubbing off, from the surface to be tested.

Additional and other objects and features of the invention will become evident from the description set forth hereinafter when considered in conjunction with the accompanying drawings.

BRIEF DESCRIPTION OF THE DRAWINGS

FIG. 1 is a schematic perspective view of a first embodiment of the liquid applying apparatus in conformity with the invention;

FIG. 2 is a vertical sectional view of a second embodiment of the liquid applying apparatus in conformity with the invention;

FIG. 3 is a transverse sectional view of the second embodiment;

DESCRIPTION OF THE PREFERRED EMBODIMENTS

Figure 4:
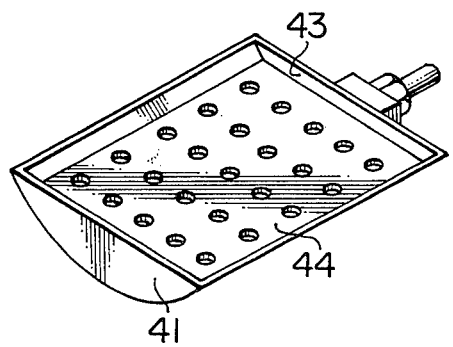
FIG. 4 is a schematic perspective view of the liquid receiving pan of the second embodiment shown in FIGS. 2 and 3.

To enable the invention to be clearly understood, the apparatus for automatically applying liquids according to the invention will be hereinafter described as being used for carrying out a penetration test for detecting defects on the surface of a structure.

Referring to FIG. 1, 2 designates a contacting member located at a forward portion of the apparatus to apply a variety of liquids to the surface of a structure to be tested and/or to remove, as by rubbing off, the applied liquids from the surface, if necessary. The contacting member 2, which is supported by a reinforcing plate 1, is liquid-absorptive and resilient and is formed of sponge or foam of rubber, polyvinyl formal (PVF) resin or other resin of high resistance to water and chemicals. The reinforcing plate 1 has secured thereto a plurality of rollers 3 supported in grooves 4' formed in a pair of rails 4 substantially in the form of a letter S for movement therein. The reinforcing plate 1 has connected to the middle thereof a wire 5 which is trained over rollers 10a and 10b and driven by an electric motor 6, so that the reinforcing plate 1 can move back and forth as the wire 5 is driven by the motor 6. Since the rails 4 are curved vertically downwardly in going toward the forward portion of the apparatus, the contacting member 2 is pressed against an article to be tested when moved forwardly and moved away from the article when moved rearwardly. A wire net 7 and a liquid receiving pan 8 are located beneath a position in which the contacting member 2 becomes stationary when moved rearwardly. The wire net 7 or liquid receiving pan 8 has one end of wires 9 secured thereto and is hung by the wires 9 which are trained over pulleys 17 and 18 are secured at the other end thereof to a bar or plate 12 connected to a forward end of a piston 11 inserted in a cylinder 10. The movement of the bar or plate 12 is guided by a pair of guide rods 12a. The reinforcing plate 1 is formed therein with a plurality of openings 13. A set of liquid nozzles 14 is mounted above a forward position in which the contacting member 2 becomes stationary and another set of liquid nozzles 15 is mounted above a rearward position in which the contacting member 2 becomes stationary, with the nozzles 14 and 15 being aligned with and disposed in close proximity to the openings 13 and directed thereto.

The basic operation of the embodiment shown in FIG. 1 and other alternative operations thereof will now be described. In the basic operation of the apparatus, when the contacting member 2 is located in the rearward stationary position, a cleaning liquid issues through the nozzles 14 to be sprayed onto the surface of an object to be tested. Simultaneously as the spraying of the cleaning liquid is carried out, a main body generally designated by the reference character $A_1$ of the apparatus is moved as a carrier $C_1$ is actuated. The carrier $C_1$ which is movable may be in the form of a mobile unit having, for example, wheels secured thereto and adapted to move along rails laid beforehand on the article to be inspected, or in the form of an actuator means of any type as desired, such as arms or levers of an industrial robot, which can be moved without coming into contact with the article to be inspected.

Upon completion of spraying the surface with the cleaning liquid, the applied cleaning liquid is removed by the contacting member 2 which is moved to its forward position. The contacting member 2 is in contact with the surface of the article when it is in the forward position as aforesaid, and rubs off both dirt and dust and cleaning liquid as it moves in sliding contact with the surface when the carrier $C_1$ moves. Cleaning of the contacting member 2 itself is performed each time the surface cleaning operation is carried out or after a series of surface cleaning operations are performed, depending on the degree to which the contacting member 2 has become soiled. Cleaning of the contacting member 2 itself is performed by moving the same to its rearward position. When the contacting member 2 is moved to the rearward position, the cleaning liquid is injected through the openings 13 formed in the reinforcing plate 1 and the bar or plate 12, guided by the guide rods 12a, is moved rearwardly of the apparatus by the piston 11 as the cylinder 10 is actuated, so that the wire net 7 is moved upwardly into pressing engagement with the contacting member 2 by the wires 9 connected at one end thereof to the bar or plate 12 and at the other end thereof to the wire net 7 or liquid receiving pan 8, so that the cleaning liquid is squeezed from the contacting member 2 together with dirt and dust. The squeezed liquid is discharged from the liquid receiving pan 8 to outside through an exhaust conduit 16 connected to the pan 8.

The aforesaid cleaning liquid and a penetrating liquid presently to be described may be of a known type. As a cleaning liquid, a solution of 98% of a petroleum base solvent and 2.0% of an anticorrosive oil may be used. As a penetrating liquid, a solution of 1.5% of an oil-soluble azo-dyestuff (carmine), 68.5% of a petroleum base solvent and 30% of fatty oil may be used.

A penetrating liquid is supplied through a conduit 20a to a change-over valve 19, from which it is fed through a conduit 14a to the forward set of nozzles 14. A conduit 20d connected to the change-over valve 19 and another conduit 20c connected to another change-over valve 19a supply the cleaning liquid to the forward set of nozzles 14 and the rearward set of nozzles 15 respectively. Another conduit 20b is for supplying a finishing liquid, subsequently to be described, to the forward set of nozzles 14 through the conduit 14a and the change-over valve 19.

Upon completion of a penetrating liquid applying operation, the applied penetrating liquid (or a layer of dried penetrating liquid) is removed from the surface of the article to be tested. The penetrating liquid removing operation is carried out by means of the contacting member 2 which is moved to the forward position. The contacting member 2 which is impregnated with a cleaning liquid rubs off the penetrating liquid. After performing the penetrating liquid removing operation, the contacting member 2 is moved to its rearward position, depending on the degree to which the contacting member 2 has become soiled, to effect cleaning of the contacting member 2 itself.

After the aforesaid series of operations have been performed, the penetrating liquid remains in defects on the surface of the article to be inspected, while the penetrating liquid on the surface of the article is removed by wiping.

Then, a finishing liquid is sprayed onto the surface of the article through the forward set of nozzles 14 as the carrier $C_1$ moves forwardly. A finishing liquid used is known per se. An example of the finishing liquid used with the aforesaid penetrating liquid is a solution of 15% of calcium carbonate powder or other white inorganic powder, and 85% of high alcohol. The high alcohol vaporizes quickly, leaving the calcium carbonate as a layer of a small thickness on the surface of the article to be inspected. As the alcohol vaporizes, the penetrating liquid in defects on the surface is sucked up by the clacium carbonate powder by capillary attraction, so that the defects are tinted by the color of the dyestuff contained in the penetrating liquid on the layer of calcium carbonate. If the penetrating liquid is of the aforesaid composition, then the defects manifest themselves in red lines or patterns. It is possible, of course, to use, as a finishing liquid, a developing agent which reacts chemically with the penetrating liquid. The aforesaid two types of liquids are merely described as examples which can be used in a testing method which enables the operator on the site of operation to readily recognize, by naked eyes, defects on the surface of an article to be tested.

After completion of the aforesaid series of operations, the contacting member 2 impregnated with the cleaning liquid is again moved to the forward position, and the carrier $C_1$ is actuated to remove the layer of calcium carbonate from the surface of the article to be tested by the contacting member 2 maintained in sliding contact with the surface. When this wiping operation is performed, the contacting member 2 is moved to the rearward position for squeezing the dirt and cleaning water from the contacting member 2, depending on the degree to which the contacting member 2 is soiled. Squeezing of dirt and cleaning water from the contacting member 2 is performed in the same manner as described with reference to the first step of cleaning the surface of the article to be tested.

In the embodiment shown in FIG. 1 and described hereinabove, the forward set of nozzles 14 has been described as being used for applying the liquids to the surface of an article to be tested and the contacting member 2 has been described as being used for rubbing off dirt and liquids. It is to be understood, however, that the invention is not limited to the use of the contacting member for carrying out wiping, and that the contacting member 2 can be used for applying the penetrating and finishing liquids to the surface of the article to be tested.

What is important is that the contacting member 2 has the function of rubbing the surface of the article to be inspected in sliding contact therewith, by virtue of its resilience. This rubbing action can, of course, be utilized for cleaning the surface, applying liquids thereto, and removing the liquids therefrom by rubbing off. The operation of cleaning the surface of the article to be inspected in the first step, the operation of applying a penetrating liquid to the surface in the second step, and the operation of applying a finishing liquid to the surface in the third step are essentially independent operation processes themselves. Therefore, the aformentioned basic method for operating the apparatus is merely for purposes of illustration and not limiting. It is to be understood that the apparatus can be operated by many modified methods without departing from the scope of the invention.

For example, if a necessary amount of liquid is fed through the forward set of nozzles 14 and openings 13 to the contacting member 2 as the latter moves to the forward position, it is possible to apply the liquid evenly to the surface of an article to be tested. This offers the advantage that no excess liquid remains on the surface of the article to be tested, so that the amount of the liquid used can be minimized.

If a liquid is sprayed onto a surface in place of being applied thereto by rubbing, many problems are raised. The sprayed liquid may scatter to the neighborhood, thereby giving rise to an air pollution problem. If a surface to be tested is highly irregular, a liquid would remain in greater amounts in depressed portions than in elevated portions. The volatile component of a liquid raises the problem of preventing explosion because such component is inflammable, control of the area in which a liquid would spread when sprayed would require adjustments of the spacing between the nozzles and the article. The aforementioned problems must be taken into consideration when a liquid is applied to a surface by spraying.

Generally speaking, it is considered that a system of direct application by rubbing is superior to a spraying system when a surface to be tested is relatively planar or narrow in area, and that the latter system is superior when a surface to be tested is greatly inclined.

The forward set of nozzles 14 is essentially used for projecting a liquid therethrough. It is to be noted that the nozzles 14 have a dual function: a function of spraying a liquid in atomized particles onto the surface of an article to be inspected, and a function of feeding a penetrating liquid to the contacting member 2. Also, the contacting member 2 has the functions of rubbing off a liquid and of applying a liquid by rubbing. Therefore, by suitably selecting and combining these functions of the nozzles 14 and the contacting member 2, any desired series of operations can be performed by the embodiment of the invention shown in FIG. 1.

FIGS. 2 and 3 show a second embodiment of the invention. A main body of the apparatus generally designated by the reference character $A_2$, with a carrier generally designated by the reference character $C_2$ supporting the main body $A_2$. The carrier $C_2$ may be of the same type as described with reference to the first embodiment of FIG. 1.

31 designates a reinforcing plate, and 32 is a contacting member. The reinforcing plate 31 is formed therein with a liquid passage 34 for receiving the supply of liquid from a liquid feeding conduit 33 and distributing the liquid to the contacting member 32. The reinforcing plate 31 is formed at one end thereof with a slider 35 which is in contact with a guide wall 36.

A cylinder 37 has inserted therein a piston rod which has secured thereto a rack 38 in meshing engagement with a pinion 39 to rotate the latter as the cylinder 37 is actuated. The pinion 39 has secured to its shaft an arm 40 which moves up and down in pivotal motion, as the pinion 39 rotates, and is connected to the reinforcing plate 31 through another pinion 45. The vertical pivotal movement of the arm 40 causes the contacting member 32 to move up and down in FIG. 2 which shows the contacting member 32 as projecting downwardly through an opening 46 formed in the bottom of the main body $A_2$. As the contacting member 32 moves upwardly, the guide wall 36 guides the movement of the slider 35. When the contacting member 32 has reached an uppermost position, the member 32 is housed in the main body $A_2$ without projecting outwardly therefrom. Upon the contacting member 32 moving to the uppermost position, a liquid receiving pan 41 is moved forwardly to close the opening 46.

A liquid receiving pan 41 includes, as shown in FIG. 4, a porous plate 44 and walls 43 supporting the plate 44. The pan 41 is curved in its bottom to conform to the curved bottom of the main body $A_2$.

The second embodiment of the invention shown in FIGS. 2-4 essentially constructed as described hereinabove operates basically as follows. A cylinder 42 is actuated to withdraw its piston rod to move the liquid receiving pan 41, which is connected to the piston rod, rearwardly of the main body $A_2$ to thereby uncover the opening 46. Then, the cylinder 37 is actuated to move the rack 38 forwardly to thereby rotate the pinion 39 counter-clockwise in FIG. 2, and move the arm 40 downwardly in pivotal movement together with the contacting member 32. The contacting member 32 projects downwardly through the opening 46 from the main body $A_2$.

After a preliminary operation described hereinabove is performed, as shown in FIG. 3, a cleaning liquid feeding conduit 48a is connected to the liquid feeding conduit 33 through a change-over valve 47. Thus, a cleaning liquid flows into the contacting member 32 through the conduit 48a, change-over valve 47, conduit 33 and liquid passage 34 in the reinforcing plate 31. While the cleaning liquid is being fed continuously or intermittently, the carrier $C_2$ is actuated to move the main body $A_2$ back and forth so as to rub the surface of an article to be tested by the contacting member 32 and remove dust and dirt therefrom. If the surface to be tested is clean, this cleaning operation may be eliminated.

After the cleaning operation is completed or while the cleaning operation is being performed, the contacting member 32 itself is cleaned when the latter has become too solid to perform its function satisfactorily. More specifically, the cylinder 37 is actuated to move the rack 38 rearwardly and move the arm 40 clockwise in FIG. 2 in pivotal movement through the pinion 39. This results in the contacting member 32 moving upwardly to its uppermost position in the main body $A_2$ in which the member 32 is housed entirely within the main body $A_2$. Thereafter, the cylinder 42 is actuated to move the liquid receiving pan 41 forwardly to close the opening 46 in the main body $A_2$ and to be disposed immediately below the contacting member 32. The cylinder 37 is again actuated to move the rack 38 forwardly and move the arm 40 counterclockwise in FIG. 2 in pivotal movement through the pinion 39. This moves the contacting member 32 into pressing engagement with the porous plate 44 of the pan 41, with the result that the liquid is squeezed from the porous plate 44. The cleaning liquid is fed through the elements 48a, 47, 33 and 34 to the contacting member 32 by repeatedly moving the rack 38 back and forth, and the contacting member 32 is moved up and down so as to squeeze the liquid from the member 32 and clean the same. The squeezed soiled water is discharged through a passage 49 in the liquid receiving pan 41.

After the cleaning operation is completed, the cylinder 42 is actuated to release the opening 46 in the main body $A_2$. Then, the rack 38 is again moved forwardly to move the contacting member 32 downwardly into engagement with the surface of the article to be tested.

Thus, it is possible either to continuously or intermittently feed the cleaning liquid again to the contacting member 32 to effect cleaning of the surface to be inspected or to feed a penetrating liquid to the surface to perform the next following operation process.

The penetrating liquid is fed through a penetrating liquid feeding conduit 48b. By actuating the change-over valve 47, the conduit 48b is connected to the feeding conduit 33, so as to feed continuously or intermittently the penetrating liquid to the contacting member 32 by way of the liquid passage 34, in the same manner as the cleaning liquid is fed. As the penetrating liquid is fed, the carrier $C_2$ moves with the main body $A_2$, so that the contacting member 32 will rub the surface of the article to be inspected to thereby uniformly apply the penetrating liquid to the surface to be inspected.

Upon completion of the penetrating liquid applying operation, the penetrating liquid applied to the surface to be tested (or a layer of the dried penetrating agent) is removed by using the cleaning liquid again. The removing of the penetrating liquid is carried out in the same manner as the removing of dust and dirt from the surface to be tested by using the cleaning liquid as described hereinabove. The cleaning liquid is fed through the conduit 48a by actuating the change-over valve 47 again.

Upon completion of the removing of the penetrating liquid or each time the contacting member 32 becomes soiled, the contacting member 32 is withdrawn into the main body $A_2$ and cleaned by the liquid receiving pan 41 which is brought into a position immediately beneath the member 32. The operation is performed as described hereinabove.

After being cleaned, the contacting member 32 is moved downwardly to project through the opening 46 out of the main body $A_2$. Then, a finishing liquid is fed through a finishing liquid feeding conduit 48c to the feeding conduit 33 by way of the change-over valve 47.

The penetrating liquid and the finishing liquid used in this embodiment may be of the same liquids as used in the first embodiment. When the same liquids as used in the first embodiment are used in combination in the second embodiment, the removing of the finishing liquid as by rubbing off is performed as a final process step.

The basic operation of the second embodiment has been described above. However, by mounting nozzles 50 on the main body $A_2$ of the apparatus, a modified operation of the apparatus can be performed. The nozzles 50 are connected, by way of a conduit 51 and a change-over valve 52, to the feeding conduits 48a, 48b and 48c.

The modified form of the embodiment is characterized in that one or both of the penetrating liquid and the finishing liquid are sprayed onto the surface of the article to be inspected through the nozzles 50. The contacting member 32 mainly performs the role of removing the liquids from the surface. However, if necessary, the contacting member 32 can apply the liquids to the surface to be tested. This modified form of operation of the embodiment is substantially similar to the basic form of operation of the first embodiment.

Figure 5:
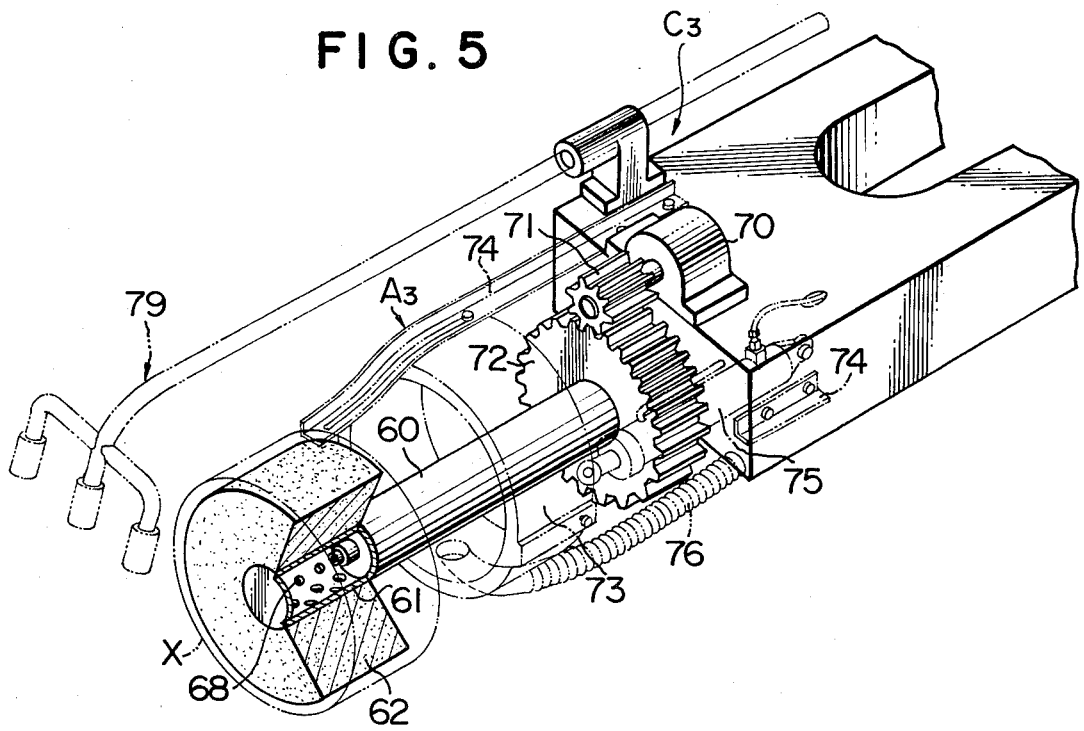
FIG. 5 is a schematic perspective view of a third embodiment of the liquid applying apparatus in conformity with the invention.
Figure 6:
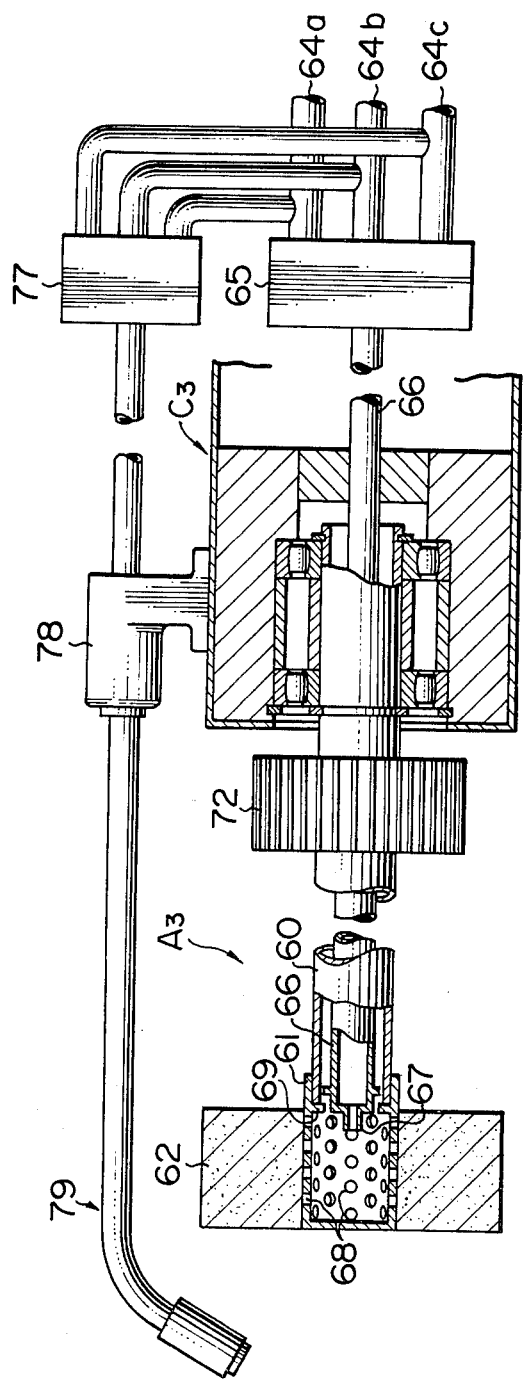
FIG. 6 is a vertical sectional view of the third embodiment.

FIGS. 5 and 6 shows a third embodiment of the invention, in which a carrier generally designated by the reference character $C_3$ is provided for supporting a main body generally designated by the reference character $A_3$. The carrier $C_3$ has connected thereto a hollow shaft 60, rotatable at high speed and low speed, which detachably mounts at its forward end a cylindrical attachment 61 and a discal contacting member 62 firmly secured to the attachment 61. The hollow shaft 60 has mounted therein a fixed conduit 66 which is secured to the carrier $C_3$ and selectively connectable to one of three liquid feeding conduits 64a, 64b and 64c by way of a change-over valve 65. The fixed conduit 66 has attached to its forward end a nozzle 67 which is located inside the attachment 61 for selectively issuing therethrough into the attachment 61 one of three types of liquids. The attachment 61 is formed in its wall with a multitude of apertures 68, and an annular ledge 69 projecting inwardly is formed in an inner wall surface of the attachment 61 in a position in which the forward end of the hollow shaft 60 is located, so that the annular ledge 69 will serve as a liquid stopper for preventing the invasion of the interior of the hollow shaft 60 by the liquids.

The hollow shaft 60 may be driven for rotation by a drive force transmitting means of any type as desired. As shown, the rotation transmitting means used comprises a gear 71 mounted on an output shaft of an electric motor 70, and a gear 72 mounted on the hollow shaft 60 and in meshing engagement with the gear 70.

In addition to the above structure, there may be provided with a cylindrical cover 73 capable of moving in reciprocatory movement along a guide rail 74 between a solid line position and a dash-and-dot line position X shown in FIG. 5, as a cylinder 75 is actuated.

The third embodiment constructed as aforementioned operates as follows. A cleaning liquid is fed from the conduit 64a to the fixed conduit 66 by way of the change-over valve 65, while the electric motor 70 is started to rotate, at a relatively low speed, the contacting member 62 attached to the hollow shaft 60. As the carrier C₃ moves, the contacting member 62 rubs the surface of an article to be tested while being kept in sliding engagement therewith, while the cleaning liquid issues through the nozzle 67 at the forward end of the fixed conduit 66 into the attachment 61. The cleaning liquid issuing through the nozzle 67 passes through the apertures 68 in the wall of the attachment 61 to be fed to the contacting member 62.

Upon completion of the cleaning operation, the contacting member 72 is cleaned. The contacting member 62 may be cleaned any time it has become soiled while the cleaning operation is being performed. In cleaning the contacting member 62, the contacting member 62 is covered with the cylindrical cover 73, and the contacting member 62 is rotated at high speed by the motor 70 while feeding the cleaning solution thereto through the fixed conduit 66, so that the filthy liquid in the contacting member 62 will be centrifugally separated by centrifugal forces. To this end, the cylinder 75 is actuated to move the cylindrical cover 73 along a groove 74 in the guide rail 75 to the position X. Thus, the cylindrical cover 73 can perform the function of preventing the scattering of the filthy liquid and discharging the same through a discharge conduit 76.

Upon completion of the cleaning operation, the cylindrical cover 73 is restored to its original position from the position X so as to expose the contacting member 62. Then, the change-over valve 65 is actuated to connect the penetrating liquid feeding conduit 64b to the fixed conduit 66, to thereby feed a penetrating liquid to the contacting member 62. The carrier C₃ is moved to rub the surface to be inspected by the contacting member 62 which is impregnated with the penetrating liquid, so as to apply the penetrating liquid to the surface to be tested.

Then, the penetrating liquid applied to the surface to be inspected (or a layer of the dried penetrating liquid) is removed as by rubbing off. In performing a wiping operation, the cylinder 75 is actuated to move the cylindrical cover 73 to the position X in which the contacting member 62 is covered with the cylindrical cover 73. The cleaning liquid is supplied through the conduit 64a and fixed conduit 66 to the contacting member 62, and the hollow shaft 60 is rotated at high speed to remove by centrifugal forces the penetrating liquid and cleaning liquid from the contacting member 62. The removing of the penetrating liquid from the contacting member 62 may be performed depending on the degree to which the member 62 is soiled. After the member 62 is cleaned, the cylindrical cover 73 is returned from the position X to its original position.

Then, the change-over valve 65 is actuated to feed a finishing liquid through the conduit 64c and fixed conduit 66 to the contacting member 62, which applies the finishing liquid to the surface to be tested by rubbing the surface. After detection of defects has been completed, the finishing liquid applied to the surface may be removed, as by rubbing off, if necessary.

The aforesaid operation is the basic mode of operation of the third embodiment. This operation is substantially equivalent to the basic operation of the second embodiment. However, it is to be understood that this embodiment is not limited to the aforesaid operation, and that changes or modifications may be made, as required, in the operation performed. For example, another change-over valve 74 is preferably provided, and a tube coupler 78 is preferably selectively connected to one of the conduits 64a, 64b and 64c by way of the change-over valve 74, with spray nozzles generally designated by the reference numeral 79 for issuing liquid therethrough in atomized particles being connectable to the tube coupler 78. The function of the nozzles 79 and the role played by the contacting member 62 when the liquids are applied by spraying through the nozzles 79 are similar to those of the corresponding parts in the second embodiment. In FIG. 5, the nozzles 79 are shown as being detached from the apparatus, but in FIG. 6 the nozzles 79 are shown as being attached to the apparatus.

Figure 7:
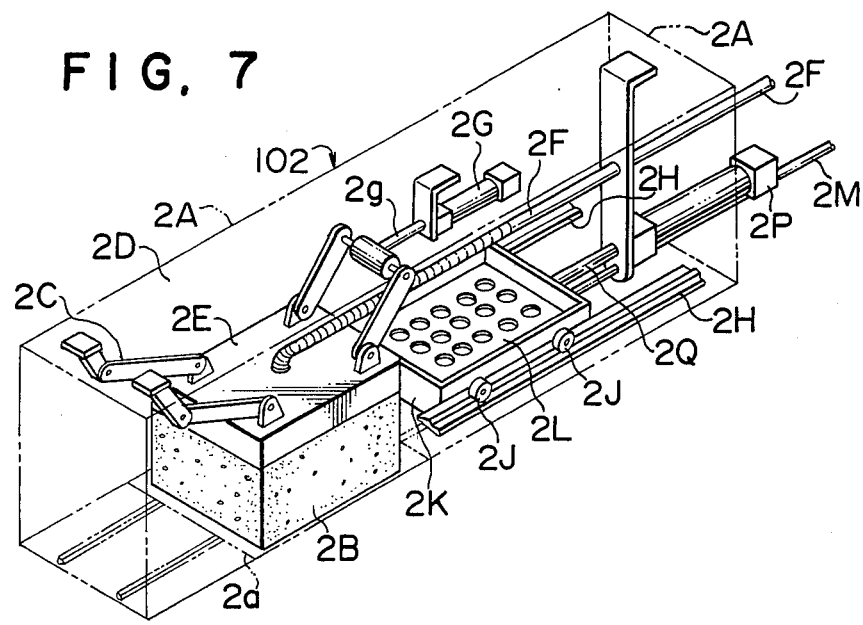
FIG. 7 is a schematic perspective view of a fourth embodiment of the liquid applying apparatus in conformity with the invention.

FIG. 7 shows a modification of the second embodiment shown in FIGS. 2 and 4. The modification shown in FIG. 7 is essentially similar to the second embodiment except that a linkage means is used in the former, in place of the rack-and-pinion arrangement 38 and 39 in the latter, for vertically moving a contacting member 2B, and that a liquid receiving pan 2A is provided with wheels 2J for movement along rails 2H in the former while the liquid receiving pan 41 is slidable by means of the cylinder 75 in the latter.

Figure 8:
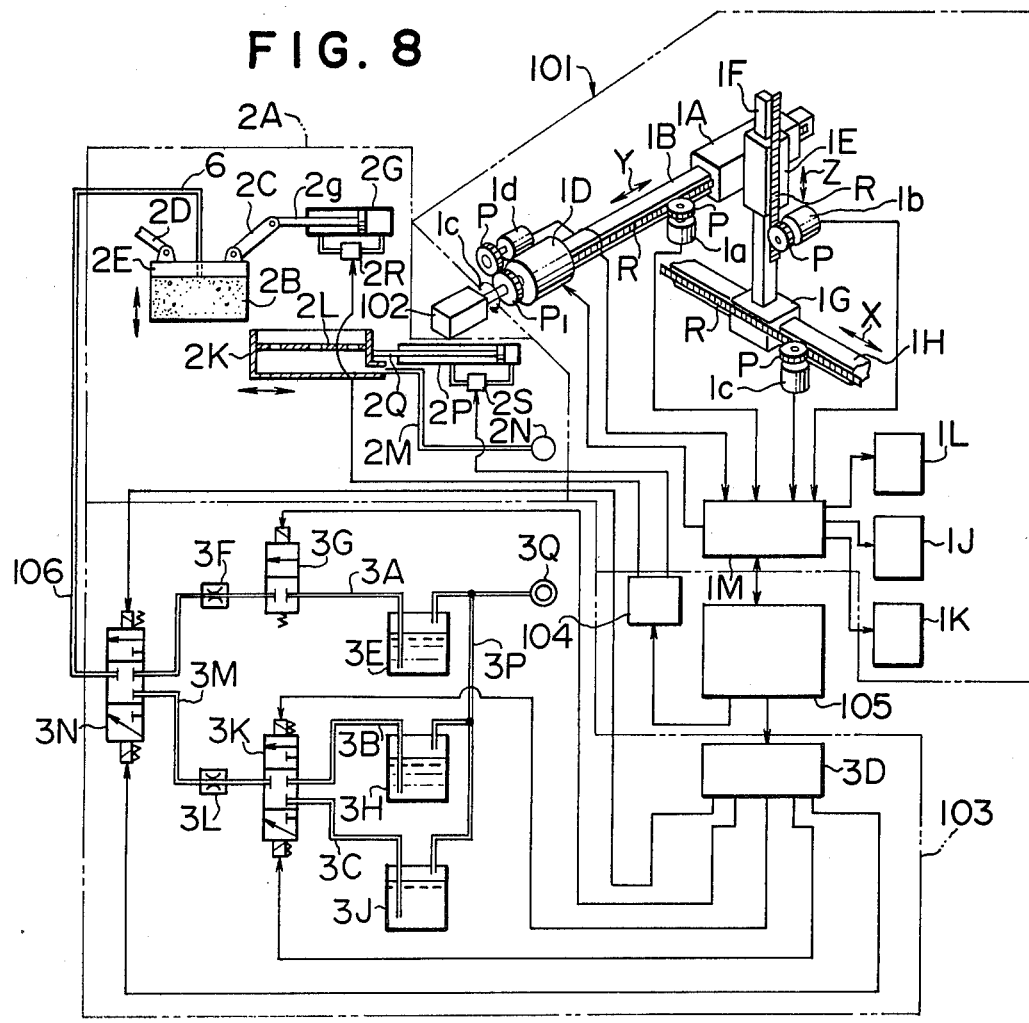
FIG. 8 is a diagram showing an example of the operating circuit and the directions of movements of various elements of the carrier of the liquid applying apparatus shown in FIG. 7.

FIG. 8 is a diagram showing an example of the operating circuit and the directions of movements of various elements of the carrier of FIG. 7. In FIGS. 7 and 8, a main body (hereinafter referred to as an applicating unit) generally designated by the reference numeral 102 is supported by the carrier generally designated by the reference numeral 101. The carrier 101 comprises a sleeve block 1A, a horizontal bar 1B supported by the sleeve block 1A for movement in Y-directions, a shaft 1C supporting, for rotation about the axis of the horizontal bar 1B, the applicating unit 102 attached to a forward end of the horizontal bar 1B, a drive means 1D, such as a pulse motor, for rotating the shaft 1C connected to the horizontal bar 1B, a sleeve block 1E secured to the sleeve block 1A and movable in Z-directions, a vertical bar 1F secured to a sleeve block 1G for guiding the movement of the sleeve block 1E in the Z-directions (vertically as shown), a fixed horizontal bar 1H for guiding the movement of the sleeve block 1G in X-directions (horizontally as shown), a drive means 1J, such as a pulse motor, for moving the horizontal bar 1B in axial movement in the Y-directions (horizontally as shown) relative to the sleeve block 1A, a drive means 1K, such as a pulse motor, for moving the sleeve blocks 1A and 1E in the Z-directions (horizontally as shown) relative to the vertical bar 1F, and a drive means 1L, such as a pulse motor, for moving the sleeve block 1G in the X-directions relative to the horizontal bar 1H. Thus, the applicating unit 102 attached to the forward end of the shaft 1C can move in a three dimensional space determined by the X, Y and Z axes, and at the same time can rotate about the axis of the horizontal bar 1B. Racks R are formed in the horizontal bar 1B and sleeve blocks 1E and 1G to feedback, to the drive means 1J, 1K and 1L, the amounts of movement (distances) of the applicating unit 102. Pulse generators 1a, 1b and 1c each provided with a pinion P which meshes with one of the racks R is fixedly mounted on a base frame, not shown. A pinion P1 is secured to an output shaft of the drive means 1D for effecting feedback for the drive means 1D, and a pulse generator 1d having a pinion P adapted to mesh with the pinion P1 is mounted at the forward end of the horizontal bar 1B. The pulse generators 1a to 1d are electrically connected to a drive means control unit 1M for collectively controlling the drive means 1D, 1J, 1K and 1L.

Meanwhile, the base frame has mounted therein a main control unit 105 for collectively controlling a valve control unit 3D, the drive means control unit 1M, and a control unit 104 for the applicating unit 102.

In FIG. 7, the applicating unit 102 includes a box-shaped casing 2A formed at its bottom with an opening 2a, and an applicator 2B mounted in the casing 2A for movement both in vertical and horizontal directions by means of a pair of linkages 2C and 2D connected to the applicator 2B through a mounting plate 2E. Connected to the mounting plate 2E supporting the applicator 2B is a liquid feeding line 2F through which a penetrating liquid and a cleaning liquid can pass into the applicator 2B by way of a liquid passage in the mounting plate 2E. Connected to the linkage 2D pivotally connected to the mounting plate 2E is a piston rod 2g of a hydraulic cylinder 2G which is effective to move the applicator 2B vertically to bring the latter into pressing engagement with the surface of an article to be tested or to release the same from pressing engagement therewith.

A pair of rails 2H parallel to the lengthwise axis of the casing 2A is laid on opposite sides of the casing 2A for supporting thereon, for movement, a liquid receiving pan 2K provided with wheels 2J. The liquid receiving pan 2K is connected to a piston rod 2Q of a hydraulic cylinder 2P secured to the casing 2A for reciprocatory movement on the rails 2H as the cylinder 2P is actuated. As shown in FIG. 7, the liquid receiving pan 2K includes a porous plate 2L located above a bottom plate of the pan 2K, and a space beneath the porous plate 2L communicates with a vacuum pump 2N through a conduit 2M.

The liquid receiving pan 2K, hydraulic cylinder 2P, hydraulic cylinder 2G for moving the applicator 2B, and the vacuum pump 2N constitute squeezing means for the applicator 2B.

Control valves 2R and 2S (FIG. 8) are mounted in pressure fluid supply lines for the hydraulic cylinders 2G and 2P respectively, and are electrically connected to the control unit 104 which is intended to control the hydraulic cylinders 2G and 2P and is in turn controlled by the main control unit 105.

Referring to FIG. 8, liquid feeding means 103 for feeding a penetrating liquid and a cleaning liquid to the applicator 2B in the applicating unit 102 is connected to the applicating unit 102 through a liquid feeding conduit 106. The liquid feeding means 103 includes a cleaning liquid feeding conduit 3A, and conduits 3B and 3C for feeding two types of applied liquids, as well as the valve control means 3D for controlling valves mounted in these conduits.

The cleaning liquid feeding conduit 3A is connected to a cleaning liquid tank 3E and has mounted therein a throttle valve 3F and a shut-off valve 3G. The penetrating liquid and finishing liquid feeding conduits 3B and 3C are connected to penetrating liquid and finishing liquid tanks 3H and 3J respectively and have mounted therein a change-over valve 3K. A throttle valve 3L is mounted in a conduit 3M which connects the change-over valve 3K to a change-over valve 3N connected, by way of the conduit 106, to the applicating unit 102. A liquid feeding pump 3Q is connected through a conduit 3P to the cleaning liquid tank 3E and the penetrating liquid and finishing liquid tanks 3H and 3J.

The operation of the apparatus constructed as shown in FIG. 7 as a fourth embodiment of the invention will now be described. When the apparatus is inoperative as shown in FIG. 7, the applicator 2B similar in construction and operation to the contacting member 2, 32, 62 is moved to an uppermost position in the casing 2A by the hydraulic cylinder 2G through the linkage means 2C, 2D, and the liquid receiving pan 2K is moved, by the hydraulic cylinder 2P, to a position adjacent the applicator 2B in its uppermost position to remain stationary therein. The change-over valves 3N and 3K and the shut-off valve 3G of the liquid feeding means 103 are kept in the positions shown in FIG. 8, so that no cleaning liquid and penetrating liquid are supplied to the applicator 2B. The valves 3N, 3K and 3G correspond to the change-over valve 47 of the second embodiment shown in FIGS. 2 and 3.

Prior to the application of a penetrating liquid to the surface of an article to be tested, the surface is cleaned. When this is the case, the main control unit 105 supplies a control signal to the valve control unit 3D which opens, upon receipt of the signal, the shut-off valve 3A of the cleaning liquid feeding conduit 3A and at the same time, moves a spool of the change-over valve 3N downwardly from its position shown in FIG. 8. Thus, the cleaning liquid in the cleaning liquid tank 3E is fed to the applicator 2B through the conduits 3A and 106. After a predetermined amount of cleaning liquid has been fed to the applicator 2B, the change-over valve 3N is restored to its position shown in FIG. 8, and substantially simultaneously as the valve 3N is actuated, the main control unit 105 supplies a signal to the control unit 104 which, upon receipt of the signal, moves the applicator 2B downwardly into pressing engagement with the surface of the article to be inspected. Then, the main control unit 105 gives instructions to the drive means control unit 1M to actuate the drive means 1D, 1K, 1L and 1J so as to move the applicator 2B along the surface of the article to be tested. As the applicator 2B moves along the surface of the article to be tested, a predetermined area of the surface is cleaned by rubbing by the cleaning liquid contained in the applicator 2B.

After the applicator 2B has moved a predetermined distance, the drive means 1D, 1J, 1K and 1L are rendered inoperative. In determining the amount of movement or the distance covered by the movement of the applicator 2B, distances are detected by the pulse generators 1a, 1b, 1c and 1d which produce pulse signals that are supplied by feedback to the control unit 1M and then to the main control unit 105 so as to calculate the total distance covered by the movement of the applicator 2B.

Upon the applicator 2B becoming stationary, the main control unit 105 gives instructions to the control unit 104 to actuate the valve 2R of the hydraulic cylinder 2G, so that the applicator 2B is moved away from the surface of the article to be tested. Then, instructions are given to the valve control unit 3D to move a spool of the change-over valve 3K downwardly from its position shown in FIG. 8 and to move the spool of the change-over valve 3N upwardly from its position shown in FIG. 8. Thus, the penetrating liquid tank 3H communicates with the applicator 2B through the conduits 3B, 3M and 106, so that a penetrating liquid can be fed to the applicator 2B. After a predetermined amount of penetrating liquid has been fed to the applicator 2B, the change-over valves 3N and 3K are restored to their positions shown in FIG. 8, so that the conduits 3M and 106 are disconnected.

Then, the main control unit 105 gives instructions to the control unit 104 to actuate the valve 2R of the hydraulic cylinder 2G, so that the applicator 2B is moved downwardly by the hydraulic cylinder 2G through the linkage 2C into pressing engagement with the surface of the article to be tested. Thereafter, the main control unit 105 gives instructions to the drive means control unit 1M to actuate the drive means 1D, 1J, 1K and 1L to cause the applicator 2B to move a predetermined distance along the surface of the article to be tested in sliding rubbing motion. After the applicator 2B has moved a predetermined distance along the surface, the main control unit 105 gives instructions to the control unit 104 to actuate the valve 2R of the hydraulic cylinder 2G so as to move the applicator 2B upwardly by the linkage means 2C, 2D. When the applicator 2B carries out the aforementioned operations, the applicator 2B is restored to its initial position in the casing 2A by the applicating unit 102 between the operation for applying the cleaning liquid to the surface of the article to be tested and the operation for applying the penetrating liquid to the surface of the article to be tested. However, the description of the operation for returning the applicator 2B to its initial position will be omitted in the interest of brevity.

After the applicator 2B is moved away from the surface of the article to be tested, the main control unit 105 gives instructions to the valve control unit 3D to open the shut-off valve 3G and to move the spool of the change-over valve 3N downwardly from its position shown in FIG. 8, to thereby communicate the conduits 3A and 106 with the applicator 2B. Thus, the cleaning liquid is fed to the applicator 2B through the conduit 106. After the cleaning liquid is fed to the applicator 2B, the control unit 104 supplies a signal to the valves 2S and 2R and actuates the same, the thereby move the liquid receiving pan 2K by the hydraulic cylinder 2P to a position which is immediately below the applicator 2B. On the other hand, the applicator 2B is moved downwardly by the hydraulic cylinder 2G into pressing engagement with the porous plate 2L of the liquid receiving pan 2K. The applicator 2B is generally moved downwardly only once. However, when it is required to move the applicator 2B downwardly several times, the main control unit 105 has only to be programmed to cause the applicator 2B to operate as desired.

As the applicator 2B is pressed against the porous plate 2L, the cleaning liquid contained in the applicator 2B is squeezed therefrom and exhausted by the vacuum pump 2N to a drain tank, not shown, through the pan 2K and the conduit 2M. As a result, the penetrating liquid in the applicator 2B is removed completely therefrom by squeezing, and the applicator 2B is ready for a developing liquid or finishing liquid to be fed thereto. The valves 2R and 2S are successively actuated by signals from the control unit 104 to move the applicator 2B upwardly away from the porous plate 2L of the liquid receiving pan 2K, by the hydraulic cylinder 2G, and to move the liquid receiving pan 2K, by the hydraulic cylinder 2P, rightwardly to its position shown in FIG. 7. Then, the valve control unit 3D produces signals to move the spools of the change-over valves 3N and 3K upwardly from their positions shown in FIG. 8, to thereby communicate the finishing liquid tank 3J with the applicator 2B through the conduits 3C, 3M and 106. As a result, the finishing liquid is fed from the tank 3J to the applicator 2B, and the applicator 2B thus impregnated with the finishing liquid is moved downwardly into pressing engagement with the surface of the article to be tested by the hydraulic cylinder 2G. Thereafter, the applicator 2B is moved a predetermined distance along the surface of the article to be tested in sliding rubbing motion. The description of the application operation will be omitted because it has already been described.

After the applicator 2B has moved a predetermined distance along the surface of the article to be tested, the applicator 2B is moved away from the surface in the same manner as described previously, and then feeding of the cleaning liquid to the applicator 2B and pressing of the applicator 2B against the porous plate 2L of the pan 2K to squeeze the liquid from the applicator 2B are automatically carried out successively.

In the fourth embodiment shown in FIGS. 7 and 8 and described hereinabove, the applicator 2B has been described as having the functions of applying a liquid to a surface and of removing the applied liquid from the surface. The invention is not limited to this specific form of the embodiment, and spray nozzles for ejecting a liquid in atomized particles may be provided, as described with reference to the first to the third embodiments, for applying a liquid to a surface to be testd, for example. When this is the case, the system shown in FIGS. 7 and 8 may be revised in such a manner that another change-over valve is mounted in the conduit 106 to selectively feed a liquid to the applicator and the spray nozzles, without departing from the scope of the invention. Liquid feeding means, which corresponds to the liquid feeding means 103, may be separately provided for the spray nozzles. Modifications may be readily made in the construction of the apparatus shown in FIGS. 7 and 8.

From the foregoing description, it will be appreciated that the present invention provides an automatic liquid applicating apparatus wherein a predetermined amount of liquid is fed to an applicator formed of sponge or other liquid absorptive material or to spray nozzles each time the applicator moves a predetermined distance along the surface of an article to be tested in sliding rubbing motion or the spray nozzles spray a liquid onto the surface to be tested. The apparatus according to the invention offers the advantage that application of a liquid to the surface of an immovable structure can be effected automatically with a high degree of efficiency and a great economic benefit.

When the apparatus offering the aforesaid advantages is used as an apparatus for applying a penetrating liquid and a finishing liquid for detecting defects on the surface of a structure by a penetration testing method, the liquid can be applied in an optimum amount, thereby preventing excessive consumption of the liquid.

It is to be understood that the invention is not limited to the specific forms of the embodiments shown and described herein and that many changes and modifications may be made therein without departing from the scope of the invention. For example, in the fourth embodiment, calculation of the amount of movement of the applicator can be effected in the main control unit 105 by utilizing the numerical signals supplied to the drive means 1D, 1J, 1K and 1L, instead of directly detecting the amounts of movements of various elements of the carrier 101. When this is the case, the pulse generators 1a, 1b, 1c and 1d which are detectors and the racks R need not be mounted in the carrier 101.

What is claimed is:

1. A liquid applying apparatus comprising:
a main body;
a carrier supporting said main body for movement;
liquid applying means mounted on said main body and comprising a surface rubbing means including a liquid-absorptive, resilient contacting member and a supporting member supporting said contacting member, and a spray nozzle means for selectively applying a variety of liquids to a surface of a structure;
liquid feeding means comprising conduit means and valve means for supplying said variety of liquids in predetermined amounts to said liquid applying means; and
liquid removing means mounted in said main body for removing liquids from said liquid-absorptive, resilient contacting member to clean the same prior to an application of a further liquid by said liquid applying means;
said liquid applying means receiving a supply of liquids through said liquid feeding means for cleaning the surface of the structure and applying desired liquids thereto by rubbing the surface by said contacting member as said carrier is actuated, and said liquid removing means being effective to remove liquids from said liquid-absorptive, resilient contacting member by performing a liquid removing operation selectively with a surface cleaning operation and a liquid applying operation performed by said liquid applying means, whereby application of the liquids can be effected automatically with a high degree of efficiency and without any loss of the liquids.

2. A liquid applying apparatus as claimed in claim 1, wherein said liquids are fed from said liquid feeding means to said resilient contacting member through said spray nozzle means.

3. A liquid applying apparatus as claimed in claim 1, wherein said liquids are fed from said liquid feeding means to the surface of the structure by spraying the liquids through the spray nozzle means directly onto the surface.

4. A liquid applying apparatus as claimed in claim 1, wherein said liquid-absorptive, resilient contacting member is cylindrical in form and said liquid applying means further comprises a hollow, cylindrical shaft connected for rotation to said carrier and detachably supporting said cylindrical contacting member at its forward end through said supporting member which is in the form of an attachment formed with a multitude of apertures in its wall, said conduit means of said liquid feeding means includes a fixed conduit extending through said hollow cylindrical shaft to slectively supply liquids to said cylindrical contacting member through said apertures in said attachment.

5. A liquid applying apparatus as claimed in claim 1, further comprising liquid reservoir means connected to said liquid feeding means for intermittently supplying said variety of liquids in predetermined amounts.

6. A liquid applying apparatus as claimed in claim 1, wherein said liquid feeding means includes a cleaning liquid feeding system and an applied liquid feeding system, and said valve means is capable of switching the apparatus between the two systems.

7. A liquid applying apparatus comprising:
a main body;
a carrier supporting said main body for movement;
liquid applying means mounted on said main body and comprising a surface rubbing means including a liquid-absorptive, resilient contacting member and a supporting member supporting said contacting member, and a spray nozzle means for selectively applying a variety of liquids to a surface of a structure;
liquid feeding means comprising conduit means and valve means for supplying said variety of liquids in predetermined amounts to said liquid applying means; and
liquid removing means mounted in said main body for removing liquids from said liquid applying means to clean the same, said liquid removing means comprises a liquid receiving pan adapted to be brought into pressing engagement with said contacting member for squeezing liquids from said contacting member;
said liquid applying means receiving a supply of liquids through said liquid feeding means for cleaning the surface of the structure and applying desired liquids thereto by rubbing the surface by said contacting member as said carrier is actuated, and said liquid removing means being effective to remove liquids from said liquid applying means by performing a liquid removing operation selectively wih a surface cleaning operation and a liquid applying operation performed by said liquid applying means, whereby application of the liquids can be effected automatically with a high degree of efficiency and without any loss of the liquids.

8. A liquid applying apparatus as claimed in claim 7, wherein said contacting member is moved to a position located within said main body when liquids are squeezed from said contacting member, and moved to a position outside said main body when liquids are applied to the surface.

9. A liquid applying apparatus as claimed in claim 8, wherein said liquid applying means further comprises rollers secured to said supporting member, a wire connected to said supporting member and to an electric motor, and a pair of rails substantially in the form of a letter S for moving said contacting member between said two positions by guiding the contacting member through said rollers, and said liquid removing means further comprises a cylinder connected to a plate and wires trained over pulleys and secured to the liquid receiving pan for moving the liquid receiving pan into pressing engagement with the contacting member to squeeze liquids therefrom when the latter is disposed in its position within the main body.

10. A liquid applying apparatus as claimed in claim 8, wherein said liquid applying means further comprises a rack-and-pinion arrangement connected to a cylinder for moving said contacting member between said two positions and bringing said contacting member into pressing engagement with said liquid receiving pan to squeeze liquids therefrom, and said liquid removing means further comprises a cylinder connected to said liquid receiving pan to move the latter between an inoperative position and an operative position in which it receives liquids removed from said contacting member.

11. A liquid applying apparatus as claimed in claim 8, wherein said liquid applying means further comprises a linkage means connected to a cylinder for moving said contacting member between said two positions, and said liquid removing means further comprises a cylinder connected to said liquid receiving pan, wheels secured to said liquid receiving pan, a pair of rails supporting said wheels for moving the liquid receiving pan so as to move the latter between an inoperative position and an operative position in which it is disposed immediately below said contacting member to squeeze liquids therefrom by the action of the cylinder, and a vacuum pump.

12. A liquid applying apparatus comprising:
a main body;
a carrier supporting said main body for movement;
a liquid applying means mounted on said main body and comprising a surface rubbing means including a liquid-absorptive, resilient contacting member and a supporting member supporting said contacting member, and a spray nozzle means for selectively applying a variety of liquids to a surface of a structure, said liquid-absorptive, resilient contacting member is cylindrical in form and said liquid applying means further comprises a hollow, cylindrical shaft connected for rotation to said carrier and detachably supporting said cylindrical contacting member at its forward end through said supporting member which is in the form of an attachment formed with a multitude of apertures in its wall;
liquid feeding means comprising conduit means and valve means for supplying said variety of liquids in predetermined amounts to said liquid applying means;
said conduit means of said liquid feeding means includes a fixed conduit extending through said hollow cylindrical shaft to selectively supply liquids to said cylindrical contacting member through said apertures in said attachment;
liquid removing means mounted in said main body for removing liquids from said liquid applying means to clean the same, said liquid removing means comprises a movable cover movable to a position in which said cylindrical shaft is rotated at high speed to remove liquids from said cylindrical contacting member by centrifugal forces so as to avoid scattering of the removed liquid;
said liquid applying means receiving a supply of liquids through said liquid feeding means for cleaning the surface of the structure and applying desired liquids thereto by rubbing the surface by said contacting member as said carrier is actuated, and said liquid removing means being effective to remove liquids from said liquid applying means by performing a liquid removing operation selectively with a surface cleaning operation and a liquid applying operation performed by said liquid applying means, whereby application of the liquids can be effected automatically with a high degree of efficiency and without any loss of the liquids.

13. A liquid applying apparatus comprising:
a main body;
a carrier supporting said main body for movement;
liquid applying means mounted on said main body and comprising a surface rubbing means including a liquid-absorptive, resilient contacting member and a supporting member supporting said contacting member, and a spray nozzle means for selectively applying a variety of liquids to a surface of a structure, said liquid-absorptive, resilient contacting member is cylindrical in form and said liquid applying means further comprises a hollow, cylindrical shaft connected for rotation to said carrier and detachably supporting said cylindrical contacting member at its forward end through said supporting member which is in the form of an attachment formed with a multitude of apertures in its wall liquid feeding means comprising conduit means and valve means for supplying liquids to said liquid applying means, said conduit means of said liquid feeding means includes a fixed conduit extending through said hollow cylindrical shaft to selectively supply liquids to said cylindrical contacting member through said apertures in said attachment, said attachment is formed on its inner wall surface with an annular ledge located in a position adjacent a forward end of said hollow, cylindrical shaft to serve as a liquid stopper, so that invasion of an interior of the hollow, cylindrical shaft by the liquids removed from said cylindrical contacting member can be avoided.

14. A liquid applying apparatus comprising:
a main body;
a carrier supporting said main body for movement, said carrier is movable in such a manner that said main body is capable of movement in a three dimensional space determined by the movement of various elements of said carrier in directions of an X-axis, Y-axis, and Z-axis;
liquid applying means mounted in said main body and comprising a surface rubbing means including a liquid-absorptive, resilient contacting member and a supporting member supporting said contacting member and a spray nozzle means for selectively applying a variety of liquids to the surface of a structure;
liquid feeding means comprising conduit means and valve means for supplying said variety of liquids in predetermined amounts to said liquid applying means; and
liquid removing means mounted in said main body for removing liquids from said liquid applying means to clean the same;
said liquid applying means receiving a supply of liquids through said liquid feeding means for cleaning the surface of the structure and applying desired liquids thereto by rubbing the surface by said contacting member as said carrier is actuated, and said liquid removing means being effective to remove liquids from said liquid applying means by performing a liquid removing operation selectively with a surface cleaning operation and a liquid applying operation performed by said liquid applying means, whereby application of the liquids can be effected automatically with a high degree of efficiency and without any loss of the liquids.

* * * * *